(12) United States Patent
Attilio et al.

(10) Patent No.: US 6,384,217 B1
(45) Date of Patent: May 7, 2002

(54) 5-CYANO-10-HYDROXY-10,11-DIHYDRO-5H-DIBENZ[B,F]AZEPINE, THE PROCESSES FOR ITS PREPARATION AND FOR ITS CONVERSION INTO 5-CARBAMOYL-10-OXO-10, 11-DIHYDRO-5H-DIBENZ[B,F]AZEPINE OR INTO 5-CARBAMOYL-5H-DIBENZ[B,F]AZEPINE

(75) Inventors: Citterio Attilio, Milan; Breviglieri Gabriele; Giacomo Bruno, both of Treviglio, all of (IT)

(73) Assignee: Farchemia S.R.L., Treviglio (IT)

( * ) Notice: Subject to any disclaimer, the term of this patent is extended or adjusted under 35 U.S.C. 154(b) by 0 days.

(21) Appl. No.: 09/788,048

(22) Filed: Feb. 17, 2001

(30) Foreign Application Priority Data

Feb. 25, 2000 (IT) .......................................... MI00A0345

(51) Int. Cl.$^7$ .............................................. C07D 223/10
(52) U.S. Cl. ....................................... 540/591; 540/592
(58) Field of Search ................................ 540/591, 592

(56) References Cited

FOREIGN PATENT DOCUMENTS

JP            11-3049     *   1/1999

* cited by examiner

*Primary Examiner*—Bruck Kifle
(74) *Attorney, Agent, or Firm*—Walter H. Schneider

(57) ABSTRACT

5-Cyano-10-Hydroxy-10,11-Dihydro-5H-Dibenzi[b,f] azepine and the process for its preparation.

17 Claims, No Drawings

5-CYANO-10-HYDROXY-10,11-DIHYDRO-5H-DIBENZ[B,F]AZEPINE, THE PROCESSES FOR ITS PREPARATION AND FOR ITS CONVERSION INTO 5-CARBAMOYL-10-OXO-10, 11-DIHYDRO-5H-DIBENZ[B,F] AZEPINE OR INTO 5-CARBAMOYL-5H-DIBENZ[B,F]AZEPINE

The present invention relates to a novel compound, namely 5-cyano-10-hydroxy-10,11-dihydro-5H-dibenz[b,f] azepine of formula (VI)

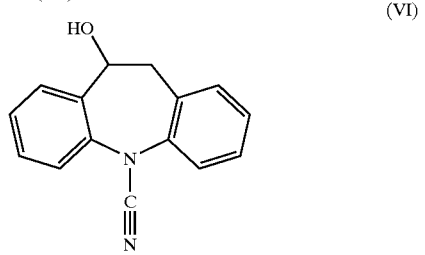

which is a starting compound for the preparation of two important pharmaceutically active compounds, respectively carbamazepine and oxcarbamazepine.

Furthermore, the invention relates to a process for the preparation of 5-cyano-10-hydroxy-10,11-dihydro-5H-dibenz[b,f]azepine, of formula (VI) characterized in that novel intermediates of general formula

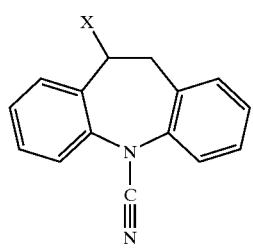

wherein X is a halogen atom or an AcO group, wherein Ac is an aliphatic or aromatic acyl residue, are subjected to hydrolysis.

Preferably, when X is a halogen atom, this is bromine or chlorine; when X is an AcO group, Ac is a $C_1$–$C_5$ aliphatic acyl residue, or a benzoyl, phenylacetyl, 2- or 3-phenyl-propionyl residue optionally substituted on the benzene ring with one or more $C_1$–$C_4$ alkyl or alkoxy groups or with one or more halogen atoms. Most preferably, Ac is an acetyl or benzoyl residue.

The invention also relates to the novel intermediates having the general formula defined above, particularly those wherein X is bromine, chlorine, acetyloxy and benzoyloxy.

In a preferred embodiment, the process according to the invention is characterized in that 5-cyano-10,11-dihydro-5H-dibenz[b,f]azepine of formula (I) is selectively halogenated or "oxygenated" at the 10-position through a radical mechanism, and 5-cyano-10-bromo-10,11-dihydro-5H-dibenz[b,f]azepine of formula (II) (X=Br), or 5-cyano-10-chloro-10,11-dihydro-5H-dibenz[b,f]azepine of formula (III) (X=Cl), or 5-cyano-10-benzoyloxy-10,11-dihydro-5H-dibenz[b,f]azepine of formula (IV) (X=OCOPh), or 5-cyano-10-acetoxy-10,11-dihydro-5H-dibenz[b,f]azepine (V) (X=OCOCH$_3$) are hydrolyzed, the final product of formula (VI) being recovered in a pure form.

The process of the invention is represented in the following reaction scheme:

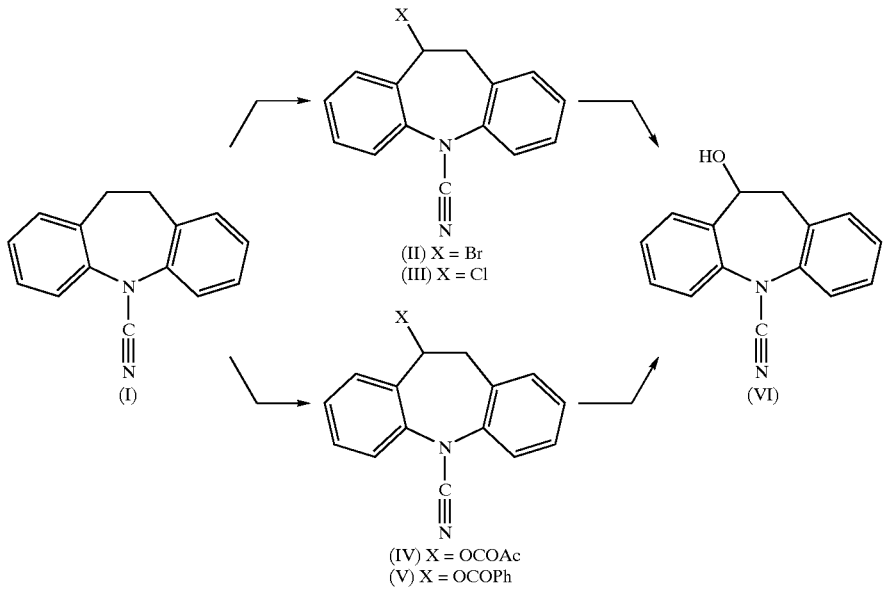

As already mentioned, the compounds (II), (III), (IV), (V) and (VI) are novel, and the compound (VI) prepared according to the present invention is a simple, inexpensive precursor for the compounds 5-cyano-10-oxo-10,11-dihydro-5H-dibenz[b,f]azepine of formula (VII), 5-carbamoyl-10-oxo-10,11 -dihydro-5H-dibenz[b,f]azepine (oxcarbamazepine) of formula (VIII) and 5-carbamoyl-5H-dibenz[b,f]azepine (carbamazepine) of formula (IX).

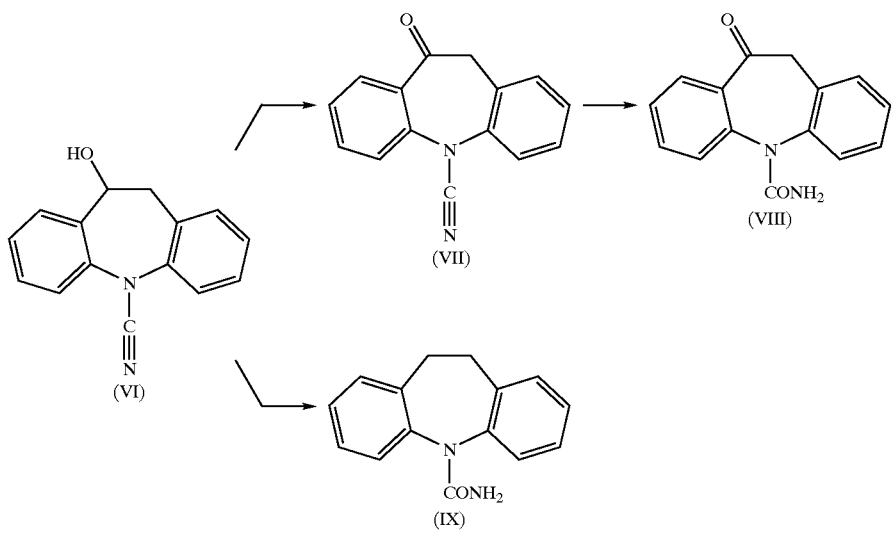

All the known processes for the preparation of compound (VIII) use 5H-dibenz[b,f]azepine unsaturated derivatives as precursors. Thus, according to DE 2,011,087, (VIII) is prepared by hydrolysis of 10-methoxy-5H-dibenz[b,f] azepine, whereas according to BE 597,793 it is prepared by hydrolysis of 10-bromo-5-acetyl-5H-dibenz[b,f]azepine, subsequent phosgenation and treatment with ammonia. JP S1 73.066 discloses the preparation of (VIII) by hydrolysis of 10-chloro-5-carbamoyl-5H-dibenz[b,f]azepine, and JP 79.138.588 by epoxidation of 5-carbamoyl-5H-dibenz[b,f] azepine, and salt-catalyzed rearrangement; according to EP 0,028,028, (VIII) is prepared from 10-nitro-5-cyano-5H-dibenz[b,f]azepine by reduction and hydrolysis. Compared with these preparation methods, which start from very expensive 9,10-unsaturated precursors and are characterized by a high number of steps, the process of the invention only comprises a limited number of steps, which can be carried out under very mild conditions with easy recycle of intermediate solvents and reagents, requires no costly reagents and provides highly pure compounds of formula (VI), (VIII) and (IX), in high yields. Furthermore, the precursor compound (I) has low cost and very good stability.

Radical functionalizations of polyalkylaromatic compounds at the side chain (halogenations and oxygenations) are known to produce complex mixtures of products with positional and substrate selectivity problems, in particular between precursors and mono-functionalized products, so that the latter are difficult to obtain with high conversions and in good yields. The most used agents are N-bromoamides, which anyway never provide selectivities above 80–85%. Even less selective are benzyl chlorination or benzyl oxygenation agents.

It has now surprisingly been found that radical bromination of the compound of formula (I) (and, to a lower, but still interesting, extent, chlorination and acyloxylation) under suitable conditions provide high selectivity, thus obtaining mono-functionalization compounds (respectively (II) by bromination, (III) by chlorination, (IV) by benzoyloxylation and (V) by acetoxylation) in very good yields, by making use of slight molar excesses of oxidizing agents (1.02–1.1), at the same time easily recovering compounds (II), (III), (IV) and (V) or subjecting directly the resulting crude compounds to hydrolysis to obtain the compound of formula (VI).

According to the present invention, compound (I) is brominated with N-bromoamides, such as N-bromosuccinimide, N,N'-dibromohydantoin, and the like, under radical initiation by means of peroxide thermal radical initiators (such as dibenzoylperoxide, di-t-butylperoxalate, and the like) or of azo-derivatives (such as azobisisobutyronitrile, azobis-1-cyclohexylnitrile, and the like), or by photochemical initiation (irradiation in the visible 400–800 nm). The reaction is carried out in a suitable solvent, which is stable under the halogenation conditions and induces no undesired side-reactions. Particularly suitable are aliphatic and aromatic halo solvents, such as $CCl_4$, $CHCl_3$, $CH_2Cl_2$, chlorobenzene, and the like. The bromoamide is used in a 1.02–1.2 molar ratio to compound (I), preferably 1.05–1.1. The ratio of starting material to solvent amount (weight/volume) can range within wide limits, 1:3 to 1:15 ratios being preferred. The reaction temperature is selected in the range of 0–150° C., preferably 20–80° C. Compound (II) can be isolated from the reaction mixture, or, preferably, it is directly hydrolyzed to obtain compound (VI).

The latter procedure is particularly convenient in that it provides a controlled hydrolysis of compound (II) and allows to recover compound (VI) from the organic phase, and hydrobromic acid and N-bromoamide from the aqueous phase, which is economically and environmentally important in that the N-bromoamide can be obtained again by oxidation of the aqueous phase, for example with alkali bromates.

According to the invention the compound (II) (isolated or crude) can in fact be hydrolyzed in an organic-aqueous diphasic system to give compound (VI). For this purpose, compound (II) is dissolved in a suitable inert organic solvent with medium-low polarity, in the above indicated ratio (or the solution resulting from bromination is used) and the resulting solution is thoroughly stirred with water. The volume ratio of organic solvent to water ranges from 1:1 to 1:10, whereas the temperature is selected from 0 to 120° C., preferably 40–80° C. Hydrolysis is continued until no more than 1–2% of (II) remains (HPLC or TLC), and it can be accelerated by the presence of polar organic compounds, such as ethers or amides, particularly polyoxyethylenes (PEG) with M.W. 300–10.000. The organic phase is separated and dried, to recover compound (VI) by conventional techniques, which compound may optionally be recrystallized from mixtures of aromatic and aliphatic solvents, esters, ethers or ketones.

The benzyl chlorination reaction under radical conditions can be carried out, according to the invention, either by use of chlorinating agents such as $Cl_2$, $SO_2Cl_2$ or N-chloroamides in the presence of thermal initiators such as those mentioned above for the bromination, or by photochemical irradiation (in the visible, 400–800 nm or nears UV). Compound (III) can be separated from by-products in useful yields, although with lower selectivity than in case of bromination. Compound (III) can be hydrolyzed to (VI) in similar solvents and ratios to those used for the bromo-derivative, at temperatures ranging from 80 to 120° C.

According to the invention, the benzyl acyloxylation reaction can be effected in organic solutions of compound (I) by decomposition (thermal, photochemical or with suitable metal salts) of diacylperoxides, such as dibenzoylperoxide or diacetylperoxide, or peresters such as t-butyl perbenzoate or t-butylperacetate, in the presence of catalytic amounts of copper(II) carboxylates having the same acid residue as the peroxocompound. Particularly suitable are aliphatic and aromatic halo solvents, such as $CCl_4$, $CHCl_3$, $CH_2Cl_2$, chlorobenzene, and the like. The peroxocompound is used in a 1.0–1.3 molar ratio to (I), preferably 1.1–1.2. The starting material to solvent ratio (weight/volume) can range within wide limits, 1:3 to 1:15 ratios being preferred. The reaction temperature is selected within the range of 0–120° C., preferably 30–90° C. The acyloxylated compound can be isolated or, preferably, it can be directly hydrolyzed to give compound (VI).

According to the invention, compound (VIII) can be obtained from compound (VII) by hydrolysis with acid agents according to the known technique (for example according the teachings of EP 0,028,028). Compound (VII) can, in its turn, be obtained from compound (VI) by oxidation with known oxidizing agents for the transformation of alcohols into ketones. In particular, it has surprisingly been found that the conversion of (VI) into (VII) is very selective and efficient when using an organic/aqueous diphasic system containing sodium hypochlorite at pH ranging from 8 to 9, in the presence of catalytic amounts (0.2–10%) of a stable nitroxide, such as 2,2,6,6-tetramethylpiperidine nitroxide (TEMPO) or 4-oxy-2,2,6,6-tetramethylpiperidine nitroxide. The used solvents are organic compounds stable to these oxidizers, in particular aliphatic and aromatic halo solvents, such as $CCl_4$, $CHCl_3$, $CH_2Cl_2$, chlorobenzene, and the like, or poorly water-soluble ethers, (methyl-tert-butyl ether or di-n-butyl ether). Sodium hypochlorite is used in concentrations ranging from 5 to 15%, and pH is adjusted with acid agents, such as $KHSO_4$, oxalic acid, dichloracetic acid, and the like. The reaction temperature is selected in the range from −10 to +60° C., preferably 0–20° C. Compound (VII) can be recovered in high yield and purity by separation of the organic phase and evaporation of the solvent, or by recrystallization from esters, such as ethyl acetate, or ketones, such as acetone or methyl ethyl ketone.

According to the invention, compound (IX) can be prepared starting from compound (VI) in a single step comprising the elimination and acid or alkali hydrolysis reactions. Alternatively, compound (IX) can be obtained by dehydration of (VIII) to give 5-cyano-5H-dibenz[b,f] azepine, and subsequent hydrolysis of the latter with acid agents.

The following examples further illustrate the invention.

EXAMPLE 1

6.60 g (0.030 mols) of 5-cyano-10,11-dihydro-5H-dibenz [b,f]-azepine (I) are stirred at 50° C. with 50 ml of $CCl_4$. The fluid suspension is added under stirring with 5.6 g (0.0315 mols) of N-bromosuccinimide of purity above 98%, then with 0.37 g (0.0015 mols) of dibenzoylperoxide. Temperature is raised to mild reflux and the mixture is stirred for a further 55 minutes controlling the formed foam, then cooled and solvent is evaporated off. The residue is suspended in toluene (15 ml) at 80° C. for 20 minutes, filtered, the solution is cooled at 0–5° C. for 1 hour, to obtain 8.2 g (83%) of 5-cyano-10-bromo-10,11-dihydro-5H-dibenz[b,f]azepine (II), m.p. 132–9 (with decomposition).

$^1$H-NMR ($CDCl_3$, δ): 3.46 (1H, dd), 3.96 (1H, dd), 5.82 (1H, dd), 7.20 (1H, dt), 7.30–7.44 (4H, m), 7.49–7.64 (3H, m). Elemental analysis: found C, 61.1; H, 3.91; Br, 27.0; N, 9.5; calculated for $C_{15}H_{11}BrN_2$: C, 60.22; H, 3.71; Br, 26.71; N, 9.36.

EXAMPLE 2

6.60 g (0.030 mols) of (I) are dissolved in 45 ml of chlorobenzene, the mixture is heated to 50° C. under stirring. The resulting solution is added under stirring with 5.6 g (0.0315 mols) of N-bromosuccinimide then with 0.49 g (0.003 mols) of azobisisobutyronitrile, stirring for 1 hour while heating at 75–80° C. The mixture is then is cooled to 40° C., added with 30 ml of water and stirred at 40° C. for 30 minutes, then heated to 80° C. for 3 hours. After decanting for 30 minutes, the aqueous phase is separated and re-extracted with 8 ml of chlorobenzene. The combined organic phases are washed with water (10 ml) and dried, then concentrated at 60° C. to 20 ml, adding 15 ml of hexane at this temperature. The mixture is cooled to 0–5° C. for 30 minutes and the separated solid is filtered, to obtain 3.68 g (52%) of 5-cyano-10-hydroxy-10,11-dihydro-5H-dibenz[b, f]azepine (VI), m.p. 117–8° C., purity>98% (HPLC).

$^1$H-NMR ($CDCl_3$, δ): 3.23 (1H, dd), 3.54 (1H, dd), 5.19 (1H, dd), 7.30–7.40 (5H, m), 7.5–7.66 (3H, m). Elemental analysis: found C, 76.1; H, 5.3; N, 11.9; calculated for $C_{15}H_{12}N_2O$: C, 76.25; H, 5.12; N, 11.86;

EXAMPLE 3

6.60 g (0.030 mols) of (I) are heated to 50° C., stirring, with 50 ml of $CCl_4$ tetrachloride. After that, 5.6 g (0.0315 mols) of N-bromosuccinimide of purity above 98%, then 0.74 g (0.003 mols) of dibenzoylperoxide, are added under stirring. The mixture is heated to mild reflux and stirred for 55 minutes, controlling the foam; then temperature is raised to 75–80° C. keeping stirring for 1 hour. The solvent is evaporated off under vacuum at 20° C. and the residue is taken up with 45 ml of 1:1 dioxane-water. The resulting solution is heated at 80° C. for 2 hours, monitoring the reaction by TLC (eluent hexane-ethyl acetate 8:2) until the bromo derivative completely disappears. The solution is evaporated under vacuum to obtain a residue (15 g) which is extracted with ethyl acetate (2×20 ml). The combined organic phases are washed with water (10 ml), dried, concentrated at 60° C. to 15 ml, then cooled at 0–5° C. for 1 hour. By filtration, 3.4 g (48%) of (VI) are recovered, m.p. 112–13° C.

EXAMPLE 4

13.2 g (0.060 mols) of (I) are dissolved at room temperature in 80 ml of $CH_2Cl_2$ under stirring, then 11.8 g (0.066 mols) of N-bromosuccinimide of purity above 98% and 0.70 g (0.003 mols) of di-tert-butyl-peroxalate are added under stirring. The reaction mixture is subjected to mild nitrogen stream for 5 minutes, then heated to 45° C. and stirred at this temperature for 85 minutes. The resulting suspension is added with 100 ml of demineralized water and 3 grams of polyethylene glycol with average molecular weight 400, then refluxed for 5 hours under strong stirring. After decanting at 30° C., the organic phase is separated, dried over 4 g of $Na_2SO_4$, filtered and the resulting solution is concentrated to 20 ml, added with 10 ml of hexane, cooled to 0–5° C. for 2 hours and filtered to obtain 8.64 g (61%) of (VI), m.p. 110–112° C.

EXAMPLE 5

150 ml of $CH_2Cl_2$, 25 g of (I) and 21 g of N-bromosuccinimide are loaded under nitrogen in a 500 ml pyrex round-bottom flask, and irradiated from the outside with a 300 watt halogen lamp, refluxing for 2 hours. 150 ml of water are added. 80 ml of $CH_2Cl_2$ are distilled off, 150 ml of toluene and 5 g of PEG 6000 are added while distilling off $CH_2Cl_2$ at inner temperature of 85–90° C. The mixture is left for 3 hours at said temperature, water is removed at 60° C., the mixture is washed with 2×50 ml of water and 30–40 ml of toluene are distilled off at 40 mm/Hg. The mixture is cooled at 0° C. for 2–3 hours, filtered, washed with 20 ml of toluene at 0° C. and air-dried at 60° C., to obtain 20.4 g of (VI) m.p. 110–111° C., with good purity. From mother liquors a further 1.8 g are recovered (overall yield 82%).

EXAMPLE 6

190 ml of chlorobenzene, 25 g of (I) and 17 g of N,N-dibromohydantoin are loaded into a 500 ml pyrex round-bottom flask, under nitrogen, and irradiated from the outside with a 300 watt halogen lamp, keeping temperature between 70 and 75° C. for 3 hours. 150 ml of water and 5 g of PEG 6000 are added, heating to 85–90° C for 2 hours. After decanting at 60° C., water is removed and the organic phase is washed with further water (2×100 ml). Chlorobenzene is evaporated off under vacuum at 5 mm/Hg and the residue is taken up with 50 ml of ethyl acetate. The mixture is cooled to 0° C., filtered and dried at 60° C. for 4 hours, to obtain 16 g of (VI), m.p. 110–111° C., with good purity.

EXAMPLE 7

190 ml of chlorobenzene and 25 g of (I) are loaded into a 500 ml pyrex round-bottom flask, under nitrogen. Afterwards, 21.2 g of N-bromosuccinimide and 2.2 g of dibenzoylperoxide are added and the mixture is heated to 85–90° C., keeping this temperature for 1.5 hours. 150 ml of water and 5 g of PEG 6000 are added, heating to 85°–90° C. for 2 hours. After decanting at 60° C., water is removed and the organic phase is washed with further water (2×100 ml). Chlorobenzene is evaporated off under vacuum at 5 mm/Hg and the residue is taken up with 50 ml of ethyl acetate. The mixture is cooled to 0° C. for 2 hours, filtered and dried at 60° C. for 4 hours, to obtain 14 g of (VI), m.p. 111–112° C., with good purity.

EXAMPLE 8

50 ml of $CH_2Cl_2$ and 5 g (0.0227 mols) of (I) are loaded into a 250 ml pyrex round-bottom flask, under nitrogen and stirring, then 2.4 g of $Na_2CO_3$ (0.045 mols) are added thereto. The mixture is cooled to 0–5° C., irradiated from the outside with a 300 watt halogen lamp while adding a 1:1 chlorine and nitrogen gaseous mixture with 6 ml/minute flow, for 3 hours, then nitrogen for 10 minutes at the same flow rate. The mixture is filtered at 30° C. and methylene chloride is evaporated off. The residue is taken up with 15 ml of hexane and 4 ml of ethyl acetate, refluxed for 15 minutes, then cooled to 0° C. for 2 hours. The solid residue is recrystallized twice with the same solvent, to obtain 2.5 g (43% yield) of 5-cyano-10-chloro-10,11-dihydro-5H-dibenz[b,f]azepine (III) with melting point 139–140° C.

$^1$H-NMR (CDCl$_3$, δ): 3.42 (1H, dd), 3.87 (1H, dd), 5.62 (1H, dd), 7.1–7.7 (8H, m). Elemental analysis: found C, 70.58; H, 4,5; N, 10.9; calculated for $C_{15}H_{12}ClN_2$: C, 70.73; H, 4.35; Cl, 11.92; N, 11.00.

EXAMPLE 9

6.60 g (0.030 mols) of (I) are dissolved in 45 ml of chlorobenzene, heating to 50° C. under stirring, then added with 0.82 g (0.003 mols) of copper(II) benzoate and 6.9 g (0.033 mols) of dibenzoylperoxide. The reaction mixture is heated to 90° C. and stirred for 3 hours, then cooled to 40° C., added with 40 ml of a 3% HCI solution and stirred at 40° C. for 30 minutes, then at 80° C. for 5 hours. 20 ml of a $NaHCO_3$ saturated solution are added to the mixture, which is stirred for 30 minutes and decanted for 1 hour The aqueous phase is separated and re-extracted with 8 ml of chlorobenzene. The combined organic phases are washed with water (10 ml), dried and concentrated at 60° C. to 20 ml, and 20 ml of hexane are added at this temperature. The mixture is cooled to 0–5° C. for 30 minutes and the solid is filtered to obtain 3.16 g (45%) of compound (VI), m.p. 112–3° C., with good purity.

The intermediate 5-cyano-10-benzoyloxy-10,11-dihydro-5H-dibenz[b,f]azepine (V) can be isolated in a 62% yield by silica chromatography with eluent hexane: ethyl acetate 85:15 before hydrolysis, m.p. 123–4° C.

$^1$H-NMR (CDCl$_3$, δ): 2.79 (1H, dd), 3.36 (1H, dd), 5.70 (1H, dd), 7.0–8.0 (13H, m). Elemental analysis: found C, 77.5; H, 4.5; N, 8.3; calculated for $C_{22}H_{16}N_2O_2$: C, 77.63; H, 4.74; N, 8.23.

Analogously, using tert-butyl peracetate and copper acetate in the same ratios as in Example 7, 5-cyano-10-acetoxy-10,11-dihydro-5H-dibenz[b,f]azepine (IV) was isolated by chromatography of the crude, before the hydrolysis, in a 70% yield, m.p. 108–19° C.

$^1$H-NMR (CDCl$_3$, δ): 2.02 (3H, s), 3.25 (1H, dd), 3.42 (1H, dd), 5.70 (1H, dd), 7.0–7.7 (8H, m). Elemental analysis: found C, 73.3; H, 5.2; N, 10.3; calculated for $C_{17}H_{14}N_2O_2$: C, 73.37; H, 5.07; N, 10.1.

EXAMPLE 10

20 g (85 mmols) of (I) are dissolved in 120 ml of $CH_2Cl_2$. The solution is cooled to 0° C. and added with 0.24 g of 2,2,6,6-tetramethylpiperidine nitroxide, then with 180 ml of 1.4M NaClO, adjusted to pH 8.3 with a $NaHSO_4$ saturated solution. The mixture is left for 1 hour at 0° C., then warmed to 20° C. for 4 hours. The organic phase is separated and washed with 50 ml of water, dried with 2 g of $Na_2SO_4$ and solvent is evaporated off. The residue is taken up with 50 ml of acetone and kept at 0° C. for 2 hours. The mixture is filtered, washed with 50 ml of cold acetone, dried at 60° C. for 4 hours to obtain 17 g of 5-cyano-10-oxo-10,11-dihydro-5H-dibenz[b,f]azepine (VII), m.p. 153–4° C., with 98.5% purity by HPLC (85% yield).

EXAMPLE 11

A 98% $H_2SO_4$ solution (10 ml) in acetic acid (40 ml) at 0° C. is added with 5 g of 5-cyano-10-oxo-10,11-dihydro- 5H-dibenz[b,f]azepine (VII) obtained as in Example 10. The mixture is stirred for 10 minutes, then kept at room temperature for 6 hours. The resulting solution is poured in 400 ml of water at 0–5° C., stirred for 30 minutes and filtered, thoroughly washing with water. The filtrate is dried at 60° C. for 3 hours, to obtain 4.8 g of 5-carboxyamido-10-oxo-10,11-dihydro-5H-dibenz[b,f]azepine, m.p. 194–5° C., 98% purity by HPLC (90% yield). The product is recrystallized from acetone:water (110 ml:19.7 ml) refluxed, added with 0.5 g of carbon and filtered through Celite. The filtrate is cooled to 0C. for 2 hours, and the precipitate is washed with 20 ml of cold acetone and dried at 60° C. for 4 hours to obtain 3.8 g of (VIII), m.p. 196–7° C., 99% purity by HPLC.

EXAMPLE 12

20 g (85 mmols) of 5-cyano-10-hydroxy-10,11-dihydro-5H-dibenz[b,f]azepine are dissolved in 200 ml of acetic acid, the mixture is cooled to 0° C., added in 20 minutes with 14 ml of 98% $H_2SO_4$, then heated at 80° C. for 120 minutes. The mixture is cooled to 0–5° C., added with 150 ml of 15% ammonia in 30 minutes, then filtered. The resulting product is recrystallized from toluene, to obtain 14.6 g of 5-carboxyamido-5H-dibenz[b,f]azepine (IX), m.p. 197–8° C., with good purity (90% yield).

What is claimed is:

1. The compound 5-cyano-10-hydroxy-10,11-dihydro-5H-dibenz[b,f]azepine of the formula

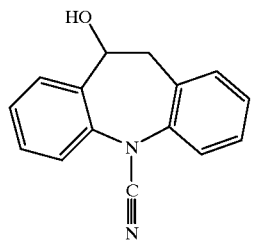

2. A process for the preparation of 5-cyano-10 hydroxy-10,11-dihydro-5H-dibenz[b,f]azepine characterized in that a compound of the formula

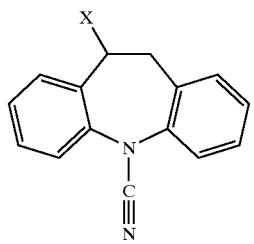

wherein X is a halogen or an AcO group, wherein Ac is an aliphatic or aromatic acyl group, is subjected to hydrolysis.

3. The process as claimed in claim 2, characterized in that the compound of the formula

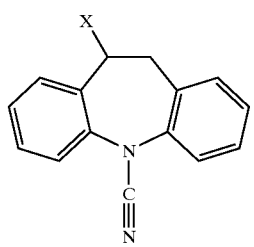

wherein X is bromine, chlorine acetoxy or benzoyloxy is subjected to hydrolysis.

4. The process as claimed in claim 2, characterized in that
a) 5-cyano-10,11-dihydro-5H-dibenz[b,f]azepine (I) is subjected to radical selective halogenation or acyloxylation at the 10-position, and
b) the resulting intermediates of the formulse (II), (III), (IV) and (V) are hydrolyzed according to the following scheme:

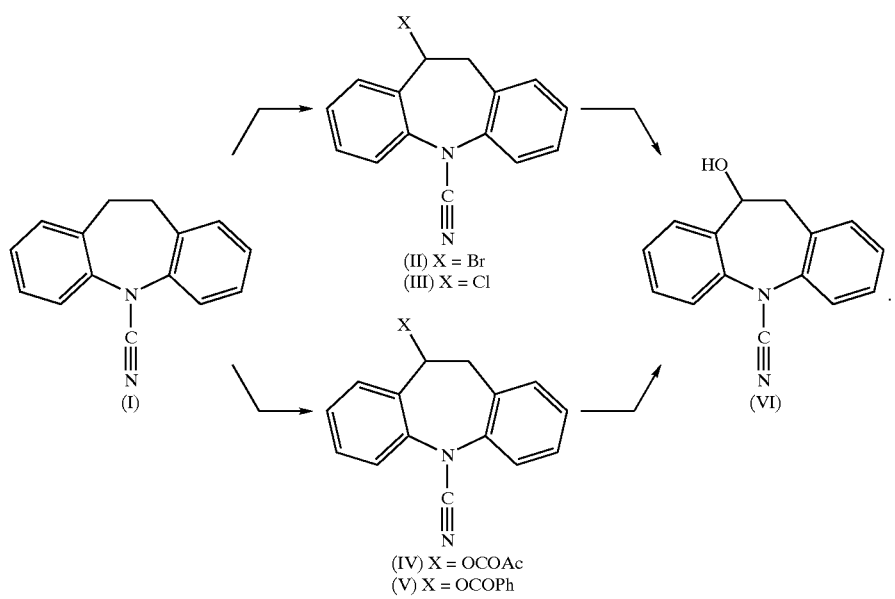

5. A process as claimed in claim 4, characterized in that the halogenation of compound (I) is carried out with a N-bromoamide selected from the group consisting of N-bromo-succinimide and N,N'-dibromohydantoin.

6. A process as claimed in claim 4, characterized in that the halogenation of compound (I) is carried out with a chlorinated agent selected from the group consisting of $Cl_2$, $SO_2Cl_2$ and N-chloroamides.

7. A process as claimed in claim 4, characterized in that the halogenation is carried out in the presence of radical initiators selected from the group consisting of peroxocompounds and azoderivatives.

8. A process as claimed in claim 7, characterized in that the radical initiator is selected from the group consisting of dibenzoylperoxide, di-t-butyl peroxalate, azobisisobutyronitrile and azobis-1-cyanocyclohexane.

9. A process as claimed in claim 4, characterized in that the halogenation is carried out through photochemical irradiation (400–800 nm or near UV).

10. A process as claimed in claim 4, characterized in that the acyloxylation is carried out by thermal, photochemical or catalytic decomposition of peroxocompounds selected from the group consisting of diacetylperoxide, dibenzoylperoxide, t-butylperacetate or t-butylperbenzoate.

11. A process as claimed in claim 10, characterized in that it is carried out in the presence of catalytic amounts of copper(II) carboxylates having the same acid residue as the used peroxocompound.

12. A process according to claim 11, characterized in that the intermediates (II), (III), (IV) and (V) are directly hydrolyzed to (VI) without being isolated from the corresponding reaction mixtures.

13. A compound of the formula

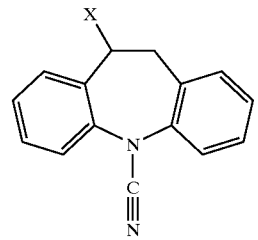

wherein X is a halogen atom or an AcO group wherein Ac is an aliphatic or aromatic acyl group.

14. The compound according to claim 13 which is 5-cyano-10-bromo-10,11-dihydro-5H-dibenz[b,f]azepine (II).

15. The compound according to claim 13 which is 5-cyano-10-chloro-10,11-dihydro-5H-dibenz[b,f,]azepine (III).

16. The compound according to claim 13 which is 5-cyano-10-acetoxy-10,11-dihydro-5H-dibenz[b,f]azepine (IV).

17. The compound according to claim 13 which is 5-cyano-10-benzoyloxy-10,11-dihydro-5H-dibenz[b,f]azepine (V).

* * * * *